United States Patent
Roberts et al.

(10) Patent No.: US 7,276,025 B2
(45) Date of Patent: Oct. 2, 2007

(54) ELECTRICAL ADAPTER FOR MEDICAL DIAGNOSTIC INSTRUMENTS USING LEDS AS ILLUMINATION SOURCES

(75) Inventors: Chris R. Roberts, Skaneateles, NY (US); Corinn C. Fahrenkrug, Liverpool, NY (US); Allan I. Krauter, Skaneateles, NY (US); Shawn A. Briggman, Syracuse, NY (US); Michael A. Pasik, Auburn, NY (US); Peter J. Davis, Skaneateles, NY (US); John R. Strom, Moravia, NY (US); Charles N. Stewart, Skaneateles, NY (US); Jon R. Salvati, Skaneateles, NY (US); Robert L. Vivenzio, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 441 days.

(21) Appl. No.: 10/393,319

(22) Filed: Mar. 20, 2003

(65) Prior Publication Data
US 2004/0183482 A1 Sep. 23, 2004

(51) Int. Cl.
*A61B 1/06* (2006.01)

(52) U.S. Cl. .......... 315/205; 600/200; 600/223; 351/221; 323/207; 323/911; 315/312; 315/362

(58) Field of Classification Search .......... 600/193, 600/197, 199, 200, 202, 245–249; 323/207, 323/221, 273, 902, 905, 911; 315/291, 307, 315/362, 205, 200 R, 312, 218, 221
See application file for complete search history.

(56) References Cited

U.S. PATENT DOCUMENTS

| 4,012,686 | A | * | 3/1977 | Heine | 323/273 |
| 5,177,424 | A | * | 1/1993 | Connors | 320/114 |
| 5,542,904 | A | * | 8/1996 | Heine et al. | 600/197 |
| 5,559,422 | A | * | 9/1996 | Fahrenkrug et al. | 323/221 |
| 5,998,925 | A | * | 12/1999 | Shimizu et al. | 313/503 |
| 6,069,440 | A | * | 5/2000 | Shimizu et al. | 313/486 |
| 6,106,457 | A | * | 8/2000 | Perkins et al. | 600/175 |
| 6,130,520 | A | * | 10/2000 | Wawro et al. | 320/114 |
| 6,211,626 | B1 | * | 4/2001 | Lys et al. | 315/291 |
| 6,305,818 | B1 | | 10/2001 | Lebens et al. | 362/184 |
| 6,547,394 | B2 | * | 4/2003 | Doherty | 351/221 |
| 2002/0038075 | A1 | | 3/2002 | Tsai | |
| 2004/0127771 | A1 | | 7/2004 | Heine et al. | |
| 2004/0252278 | A1 | | 12/2004 | Williams | 351/221 |

FOREIGN PATENT DOCUMENTS

DE   201 19 187   4/2002

* cited by examiner

*Primary Examiner*—Haissa Philogene
(74) *Attorney, Agent, or Firm*—Marjama & Bilinski LLP

(57) ABSTRACT

An adapter for permitting a medical diagnostic instrument having an illumination source including at least one LED (light emitting diode) to be used with a power supply normally configured for use with a diagnostic instrument having at least one incandescent lamp as an illumination source. The adapter includes circuitry for compensating LED specific characteristics for permitting the power supply to be used with the LED.

80 Claims, 11 Drawing Sheets

ELECTRICAL ADAPTER FOR MEDICAL DIAGNOSTIC INSTRUMENTS USING LEDS AS ILLUMINATION SOURCES

FIELD OF THE INVENTION

The following application generally relates to the field of illumination, and more particularly to an LED illumination system intended for use with hand held medical diagnostic instruments, such as those used in a physician's or health care provider's office, or other medical environments.

BACKGROUND OF THE INVENTION

Many manufacturers of hand-held medical diagnostic instrument products including otoscopes, ophthalmoscopes, et al., such as those from Heine Inc., Welch Allyn, Inc., and Keeler Instruments, among others, have long since utilized miniature incandescent lamps, such as halogen and xenon lamps, as illumination sources. These lamps are typically provided within the handle or the head of the instrument and utilize fiber optic bundles or other optical means to transmit the light from the miniature lamp to the tip opening of the diagnostic instrument, such as an ophthalmoscope, otoscope, or similar device.

Power sources for these lamps are typically either wall mounted or are portable, in the form of batteries provided in the instrument handle and having a nominal voltage of approximately 2.5 or 3.5 volts. These voltages are convenient values, since they match both a stacked arrangement of two or three Nickel cadmium batteries and 3.5 volts in particular is favored since it is also the voltage of a single lithium ion cell. Examples of instruments having same are described, for example, in U.S. Pat. Nos. 4,012,686, 5,559,422, 5,177,424, and 5,542,904.

More recently, there has been considerable interest in the field in light emitting diodes (LEDs) as a potential substitute for miniature incandescent lamps. White versions of these LEDs, such as those described, for example, in U.S. Pat. Nos. 6,069,440 and 5,998,925, among others, the entire contents of which are herein incorporated by reference, provide better illumination capability than predecessor LEDs and are therefore coveted for a myriad of applications due to their longer life, resistance to shock and impact loads, cooler operating temperatures and alternative spectral content as compared with the afore mentioned miniature incandescent lamps. Moreover and adding LEDs in general, such as color LEDs, provide additional benefits such as spectral tuning, IR, spectrally specific illumination, and the like.

It is a general desire in the field that future product improvements incorporating white LEDs as illumination sources be compatible with both the mechanical and electrical features of existing power supplies to which these instruments are interconnected. There are, however, a number of significant differences which must be recognized in the incorporation of the above illumination devices into any previously known medical diagnostic instrument. For example, white LEDs, such as those described above, experience a large variation in forward voltage as compared with miniature incandescent lamps, as well as significant differences in current versus light output and color characteristics. There are also mechanical issues relating to the incorporation of any adapter into a medical diagnostic instrument.

In summary, there is a need to develop an adaptive means which can be mechanically, optically and electrically incorporated into the design of a hand-held medical diagnostic instrument so as to permit an instrument having LEDs as an illumination source to be readily used with a variety of existing power supplies and charging apparatus. There is an additional need to enable current instrument heads which formerly used miniature incandescent lamps to utilize white or color LEDs with these existing power sources.

SUMMARY OF THE INVENTION

It is therefore a primary object of the present invention to overcome the above-noted deficiencies of the prior art.

It is another primary object of the present invention to develop electrical adapters that can permit LEDs, such as white LEDs, to be utilized in existing known hand-held medical diagnostic instruments without requiring major configuration changes to already existing power supplies and/or electrical charging apparatus.

It is yet another primary object of the present invention to provide an electrical adapter which permits white LEDs to be utilized in already existing hand-held diagnostic instruments, such as otoscopes, without significantly impacting the mechanical and/or optical function or design of the instruments.

Therefore and according to a preferred aspect of the invention, there is provided an electrical adapter for use with a medical diagnostic instrument typically configured with an incandescent lamp as an illumination source and a power supply for powering said incandescent lamp, said adapter having means for permitting at least one LED to be used as the illumination source for said instrument while permitting said existing power supply to used therewith.

Preferably, means are included for compensating LED-specific characteristics for permitting the power supply to be used with the medical diagnostic instrument. The adapter preferably includes an AC to DC converter in order to compensate for variations in forward voltage of at least one white LED used as an illumination source and to effect polarity discrepancies. The AC to DC converter can consist of, for example, at least one diode bridge or a MOSFET switch. The adapter also preferably includes means for compensating LED specific differences such as current, voltage boost, regulation, and color sense, thereby permitting use of the diagnostic instrument having at least one white LED with already existing power supplies and/or battery charging apparatus.

According to one preferred embodiment, the LED electrical adapter can be disposed within the head of the diagnostic instrument so as to permit interchangeability of illumination devices; that is, in which one interchangeable instrument head can include a miniature incandescent lamp and another interchangeable head includes a least one white LED and an electrical adapter permitting the LED to be utilized with the remainder of the instrument whether the instrument includes a wall mounted power supply or batteries.

Alternatively and according to yet another preferred embodiment, the LED electrical adapter can be fitted in lieu of a conventional battery within the instrument handle. The adapter, in fact, can be manufactured and sized so as to effectively replace a battery within the handle.

According to yet another preferred aspect of the invention, there is provided in combination, an adapter for use with a medical diagnostic instrument, said instrument including a power supply, electrically configured for powering an incandescent bulb as an illumination source, said instrument including an instrument head, a hand-grippable handle and at least one LED disposed in said instrument as the illumination source of said instrument, said adapter including means for electrically interconnecting said power supply and said at least one LED for effectively energizing said at least one LED.

According to still another preferred aspect of the present invention, there is provided a method for adapting a medical diagnostic instrument for use with at least one LED as an illumination source, said instrument including a power supply typically only electrically configured for energizing an incandescent lamp as an illumination source, said method comprising the steps of:

adding an adapter to at least one of said instrument head, said instrument handle, and said instrument power supply; and electrically connecting said adapter to said power supply and to said at least one LED to energize same without modification to said power supply.

According to yet another preferred aspect of the invention, there is provided a method for adapting a existing medical diagnostic instrument so as to incorporate at least one LED as an illumination source, said existing instrument including a power supply for energizing a miniature incandescent bulb as an illumination source, said instrument including an existing instrument head and a existing instrument handle wherein said existing instrument head and said existing instrument handle include mating interconnecting ends which interlock said instrument head and said handle in a mechanical interconnection while simultaneously maintaining an electrical interface between said incandescent lamp and said power supply, said method including the steps of:

attaching an adapter between said instrument head and said instrument handle, said adapter including means for electrically interconnecting at least one LED and said power supply as well as means for mechanically interconnecting said instrument head and said instrument handle; and mounting said at least one LED in one of said adapter and said instrument head.

An advantage of the present invention is that the herein described electrical adapter permits a number of hand-held medical diagnostic instruments to be used with any previously existing power supplies or battery charging apparatus used therein without significant modification.

Still another advantage of the present invention is that the herein described electrical adapter permits each of the advantages of LEDs to be brought to the diagnostic instrument. These advantages which include longer lamp life, longer battery life, reduced maintenance, and higher reliability without significantly impacting cost which heretofore could not easily be brought to the instrument without significant redesign of the electrical system.

These and other objects, features, and advantages will become readily apparent from the following Detailed Description which should be read in conjunction with the accompanying drawings.

DETAILED DESCRIPTION

The following description relates in general to an LED electrical adapter that can be used in a hand-held medical diagnostic instrument, such as an ophthalmoscope, otoscope, vaginoscope, and the like, though the embodiments described herein detail a specific instrument, namely an otoscope.

Figure 1:
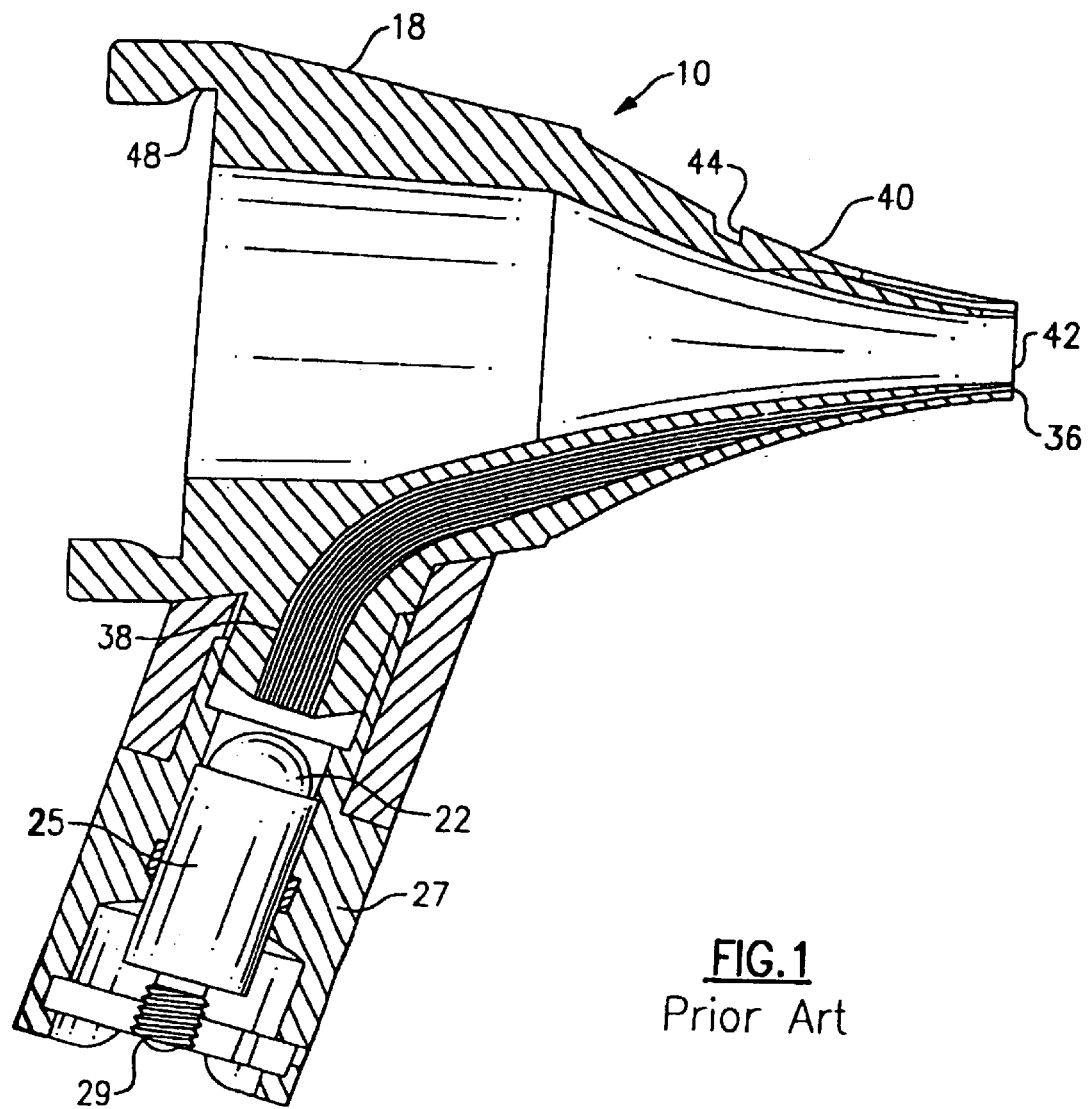
FIG. 1 is a partial side section view of the head of a prior art medical diagnostic instrument.
Figure 2:
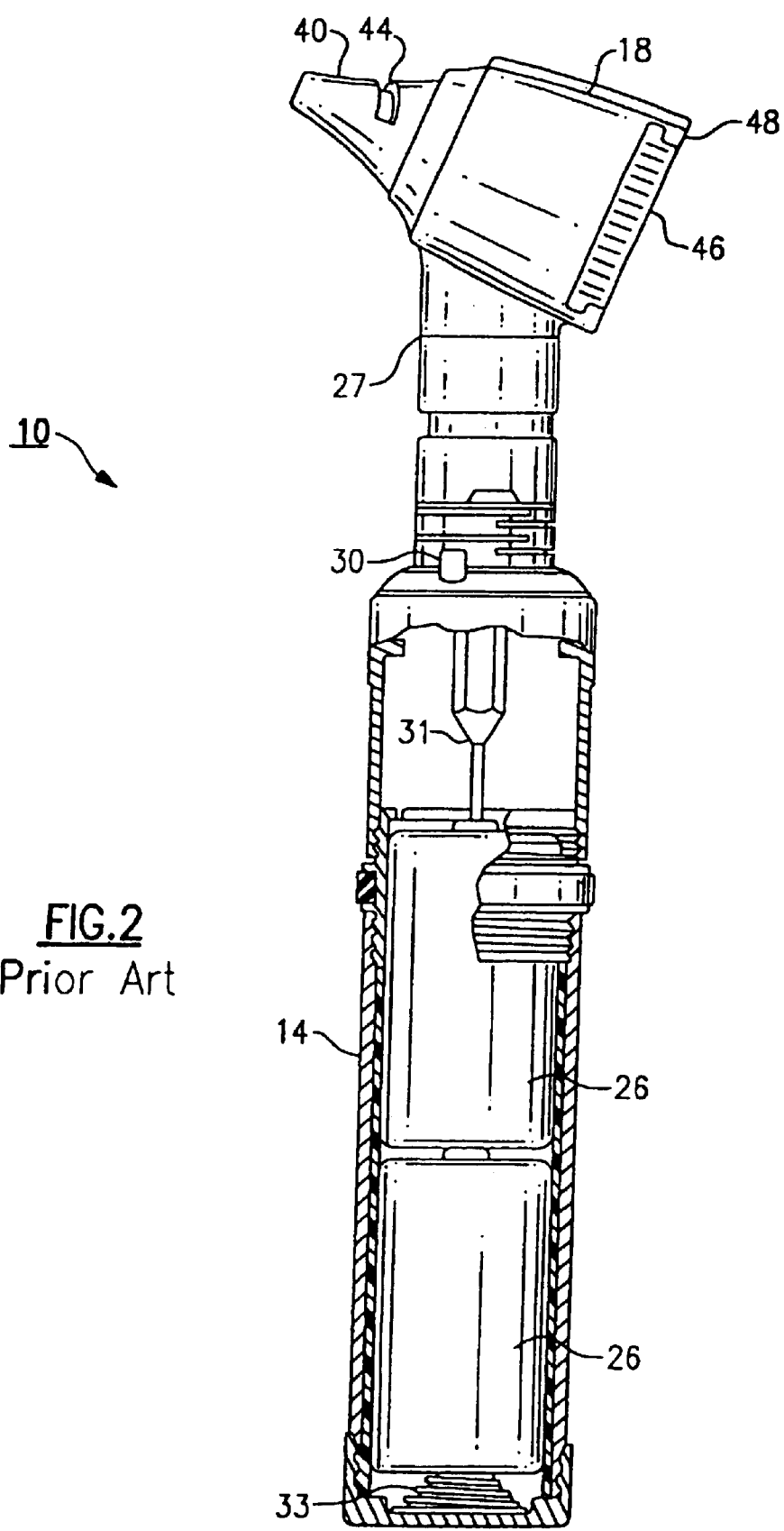
FIG. 2 is a partial side sectioned view of the medical diagnostic instrument of FIG. 1, including a portable battery power source.

Prior to discussing the invention and referring to FIGS. 1 and 2, there is first shown a medical hand-held diagnostic instrument that is already known in accordance with the prior art. In this instance, the diagnostic instrument 10 is a conventional otoscope, used for the examination of the outer ear, including the tympanic membrane. This instrument 10 generally includes a hollow instrument handle 14 and an instrument head 18 that is attached to the top of the handle. The instrument head 18 is hollow and includes a frusto-conical tip portion 40 onto which a disposable speculum (not shown) is fitted in a conventional manner, such as a bayonet 44. The speculum is sized for fitting a predetermined distance into the ear canal of a patient, the tip portion 40 having a distal tip opening 42. An eyepiece 46 attached to the proximal end 48 of the instrument head 18 forms an optical path with the distal tip opening 42 through the hollow instrument head 18 to permit viewing of the medical target.

A miniature incandescent lamp 22, such as a halogen or xenon lamp, is provided in a lamp housing 25 that is disposed in a base 27 of the instrument head 18, the lamp being electrically connected through a contact 29 and a vertically extending pin 31 to a series of stacked Nickel cadmium batteries 26 that are retained in a bottom compartment of the instrument handle 14 for energizing the lamp 22. The instrument handle 14 also contains a bottom or lower contact spring 33. An adjustable voltage control 30 located on the exterior of the upper portion of the instrument handle 14 selectively adjusts the amount of illumination output provided by the miniature lamp 22.

In addition to the above and referring to FIGS. 4–7, an effective mechanical interface is essential in order to maintain electrical contact between a miniature incandescent lamp contained in the head in the manner detailed above and the contained power supply. A pair of prior art instruments 10A, 10B therefore each include a mechanical interface between the instrument head 18A, 18B and the upper end of the instrument handle 14A, 14B such that when the instrument head is attached to the handle that the above electrical connection is maintained between the lamp and the power supply for the instrument.

Figure 6:
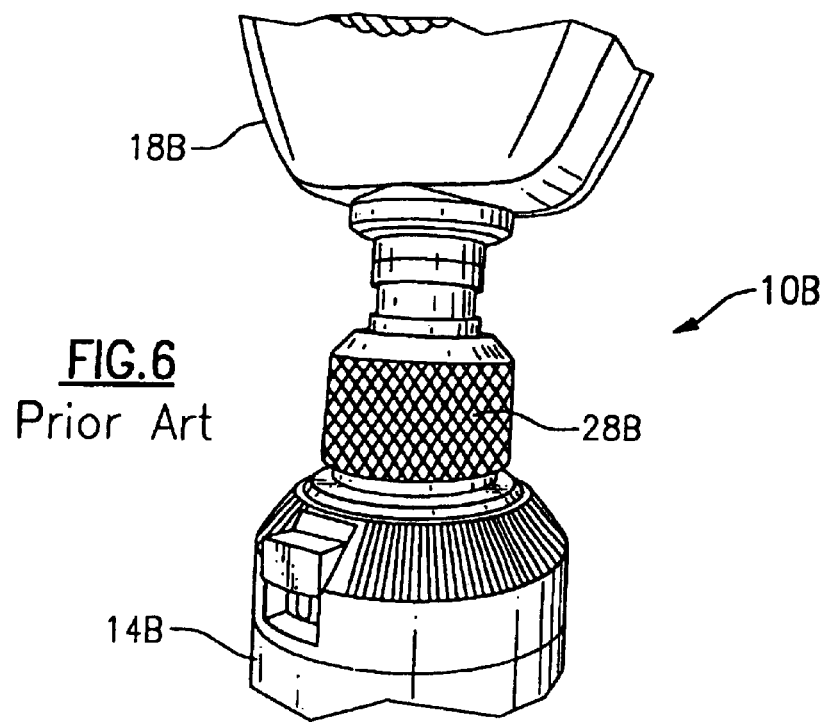
FIG. 6 is a partial side view of the interconnection between another prior art instrument head and instrument handle.
Figure 7:
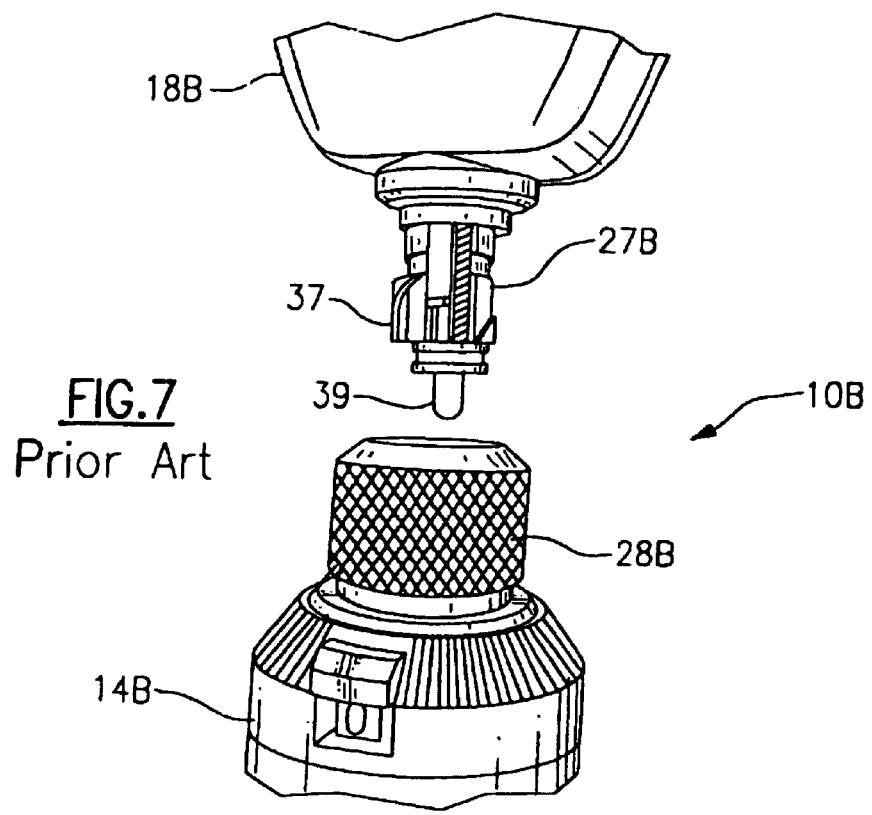
FIG. 7 is an unassembled view of the instrument of FIG. 6.

In the prior art examples illustrated in FIGS. 4–7, each of the instruments employ a form of a bayonet connection. In the instrument according to FIGS. 4 and 5, the base 27A of the instrument head 18A includes an interior set of slots (not shown) for engaging a circumferential set of ears 32 (only one being shown) provided on the exterior of the upper portion 28A of the handle 14A. A functionally similar instrument is shown in FIGS. 6 and 7 for an ophthalmoscope in which the base 27B includes a set of ears 37 for engaging a corresponding set of slots located in the upper portion 28B of the instrument handle 14B to permit the electrical contact 39 to be placed into electrical contact with the power supply of the instrument to permit illumination of the lamp disposed within the base 27B. Other suitably similar interfaces can be utilized as these depicted are intended only to be exemplary. In addition, it is known that by maintaining these mechanical and electrical interfaces/connections that various instrument heads and/or handles, including those from different manufacturers, can be combined in a single hand-held instrument.

Figure 3:
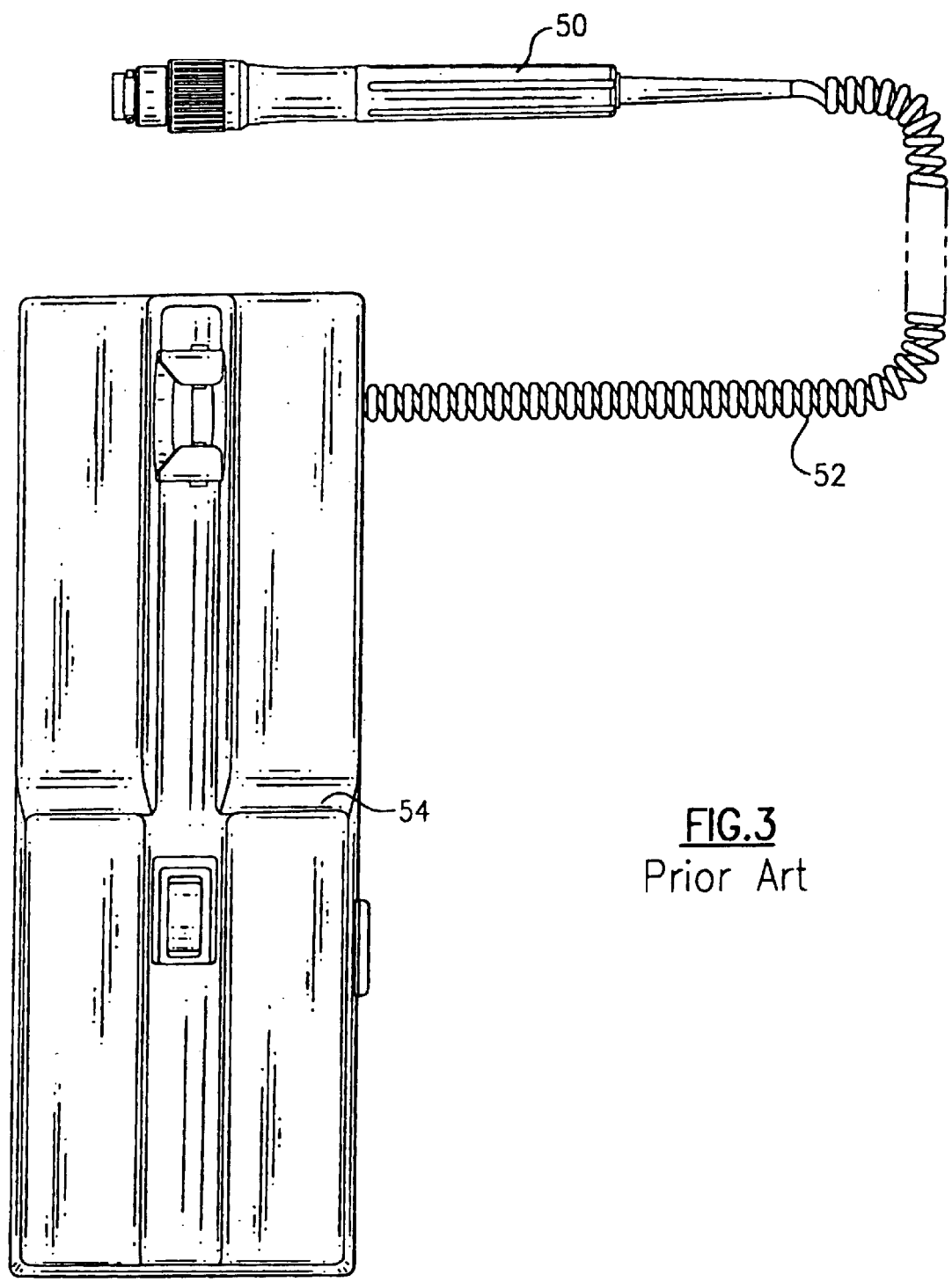
FIG. 3 is a front view of another prior art medical instrument including a wall-mounted power supply.
Figure 4:
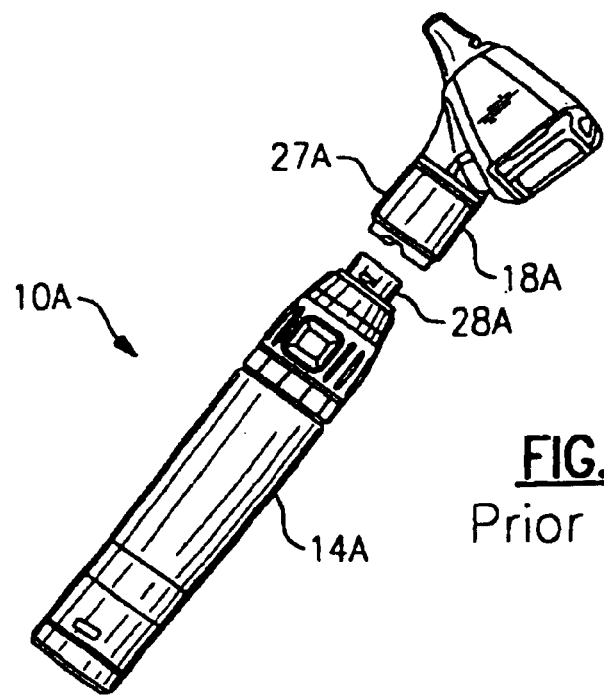
FIG. 4 is a side perspective view of a prior art diagnostic instrument illustrating the interconnection between an instrument head and the instrument handle/power supply.
Figure 5:
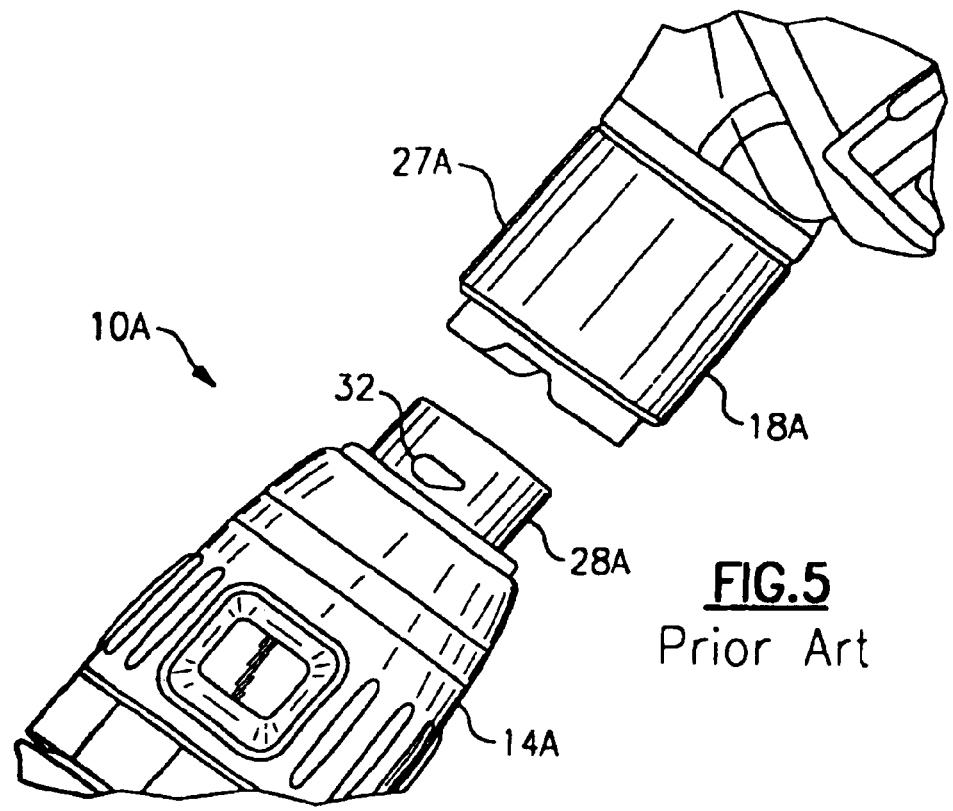
FIG. 5 is an enlarged side perspective view of the instrument head/handle-power supply interconnection of FIG. 4.

Alternately and in lieu of batteries, a hand-held medical diagnostic instrument handle 50 can be tethered by means of a cord 52 directly to a wall transformer or similar power supply 54, such as shown in FIG. 3. In each particular instance and referring to FIG. 1, a series of optical fibers 38 extend from the miniature incandescent lamp 22 through the base 27 of the instrument head 18, to a bundle of light transmitting ends 36 or other optical means that are disposed at the distal tip opening 42 in order to provide illumination of the medical target (e.g., the tympanic membrane). One typical wall transformer is further described in U.S. Pat. No. 5,559,422, incorporated herein in its entirety.

Figure 8:
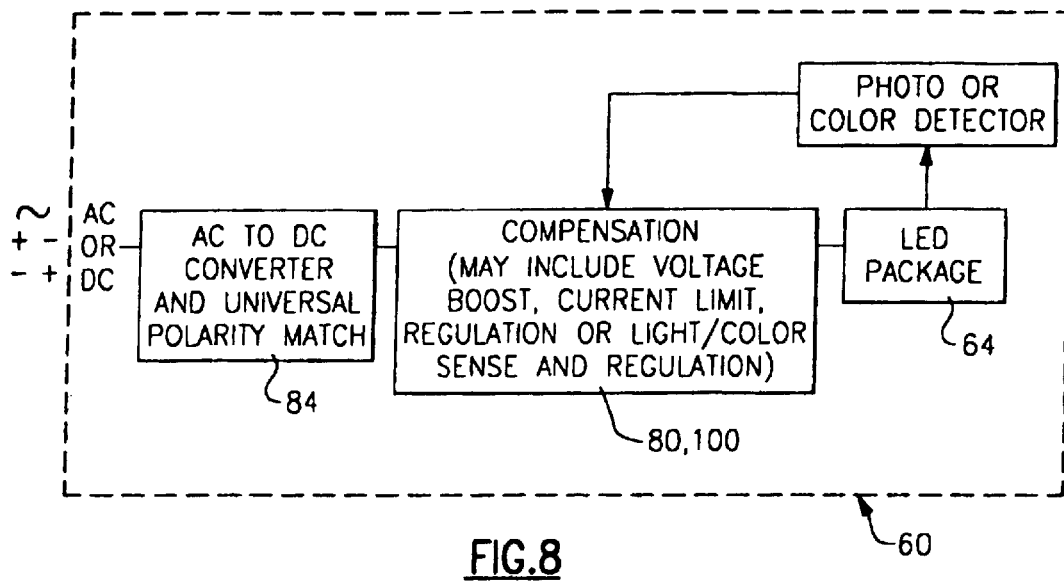
FIG. 8 is a schematic block diagram of an LED electrical adapter made in accordance with the present invention.

With the preceding background and referring now to FIG. 8, there is shown a block diagram of an LED electrical adapter 60 made in accordance with a preferred embodiment of the present invention. This electrical adapter 60 includes a number of primary features that are required in order to permit already existing power supplies, such as those shown in FIGS. 1–7, to be used in conjunction with at least one white LED package 64 that would be substituted for the miniature incandescent lamp 22, FIG. 1, in a medical diagnostic instrument.

As will be apparent from the following discussion, the mechanical and electrical design of the inventive adapter can assume a plurality of electrical, mechanical and electrical configurations covered in general by all or some features of the block diagram of FIG. 8, permitting the adapter to be used in conjunction with literally any existing power supply that provides power to an incandescent lamp-equipped medical diagnostic instrument.

In general, the LED electrical adapter 60 includes a voltage conversion portion 84 and a compensation portion 100. Each of these features will now be described in greater detail. It should be noted that for illustration purposes that the compensation portion is presumed to be a current compensation portion, although other characteristics such as voltage, light output and/or color compensation are similarly implemented.

First, the voltage conversion portion 84 herein is an AC or DC converter which can be constructed, for example, as a simple diode bridge so as to provide proper selection of the forward voltage drop of at least one white LED package 64. Alternately, there are a number of so-called "no drop" MOSFET switches, such as those manufactured by Vishay-Siliconix, among others, could preferably facilitate the voltage conversion with minimal loss in power. Provision of this conversion portion 84 permits both AC and DC power supplies to utilized. In addition, any polarity mismatch between the LED package 64 and the previously utilized miniature incandescent lamp 22 would also be corrected using this converter portion.

That is to say, while miniature incandescent lamps are unaffected by opposite polarity from a power source. LEDs require unipolar DC current in order to illuminate.

The current compensation portion 100 can include each of the following: a general current compensation means 104 for provided a limited maximum current, and a high/low stopper regulator 108.

As far as simple current compensation is concerned, a resistor or a PTC (positive thermal coefficient e.g., thermistor) can be used, though it is believed this is not the optimal solution. There are two reasons for this belief. First, there are variabilities between LEDs in terms of output versus current. Therefore, this "solution" provides partial compensation to an "average" white LED in average conditions. Additionally, this form of current compensation may not adequately compensate under low and high supply voltage conditions because the resulting differential voltage between the power source and the LED forward voltage will be directly translated into current difference when using a PTC or resistor as the compensating element. In some instances, the LED forward voltage will be higher than the source voltage and therefore no conduction will occur at all. For instance, a typical 3.5 volt battery power handle ranges between 3.0 volts and 4.2 volts and a typical white LED (such as, for example, a Lumileds Luxeon LXHL-MWIA) has a forward voltage of between about 2.55 volts and about 3.99 volts. These low voltage conditions would occur as the batteries within the instrument handle discharge, or with low line or power supplies that are set at the low end of their manufacturing tolerances.

In addition, high voltage conditions could conversely cause excessive current to flow, resulting in very poor color or in the extreme, failure of the device itself. These high voltage conditions would occur with new, fully charged batteries, or at high line of power supplies set at the high end of manufacturing tolerances.

Regulating/limiting systems for current compensation can include for example, linear regulators, such as, for example, a National Semiconductor LM1117. Alternately, a bimetallic switch can be applied which can be set to create a duty cycle which averages a corrected current in order to produce a stable consistent output as long as the voltage provided by the power source is sufficiently above the forward voltage of the LED.

Figure 9:
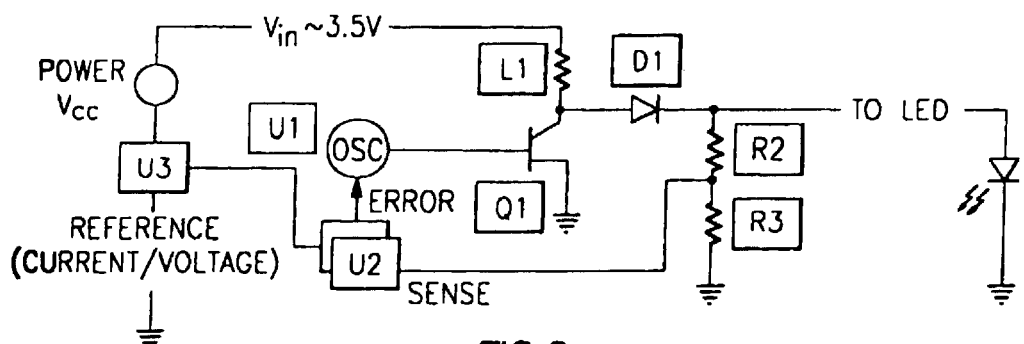
FIG. 9 is an electrical circuit diagram of an embodiment of the LED electrical adapter of FIG. 8.

Referring to FIG. 9, a circuit is herein described that controls the voltage to an LED which is used in lieu of a miniature incandescent bulb. As will be noted below and with relatively small modification, the circuit can further be configured to control the light output of the LED or the color output of the LED by selecting the appropriate detector (photodiode with or without filter) and connecting the detector to the sense feed line. The voltage control circuit of FIG. 9 functions as follows:

An oscillator (U1) is assumed to be a voltage controlled oscillator having a base frequency and a duty cycle that is a function of the input voltage. There are many PWM (pulse width modulation) type devices available, and this circuit does not rely on any particular such device. Upon initial power up of the circuit, the voltage across a pair of resistors (R2) and (R3) would be zero, and the sense voltage would be zero. Once a comparator (U2) powers up, the sense voltage (zero at start) will be compared with the reference (U3) and a positive error signal will be generated. This error is fed to the oscillator (U1) which increases its on time cycle, thereby driving transistor (Q1) to turn on. The preceding causes current to flow through an inductor (L1) and stores energy as an electromagnetic field. During the "off" cycle of the oscillator (Q1) turns off and all current is then fed forward into a diode (D1). This feeding creates a voltage and drives current into the LED when the voltage becomes higher than the LED threshold (forward voltage) which is sensed via a pair of voltage dividers (R2) and (R3). If this voltage remains lower than the reference (U3), the error comparator (U2) continues to generate a positive error and the oscillator continues to increase its pulse width which increases the energy which is stored in (L1), and consequently the output voltage into the LED. When the output and therefore the sense voltage becomes higher than that of the reference (U3), the error comparator (U2) generating a negative error signal which decreases the oscillator on time to reduce the output voltage. This process continues and maintains the output close to the reference voltage that is selected. The reference voltage is chosen to be the optimum setting for LED operation.

Figure 10:
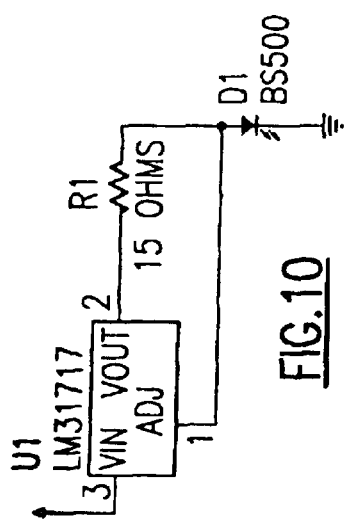
FIG. 10 is an electrical circuit diagram of a current compensation portion of the LED electrical adapter of FIG. 8.
Figure 11:
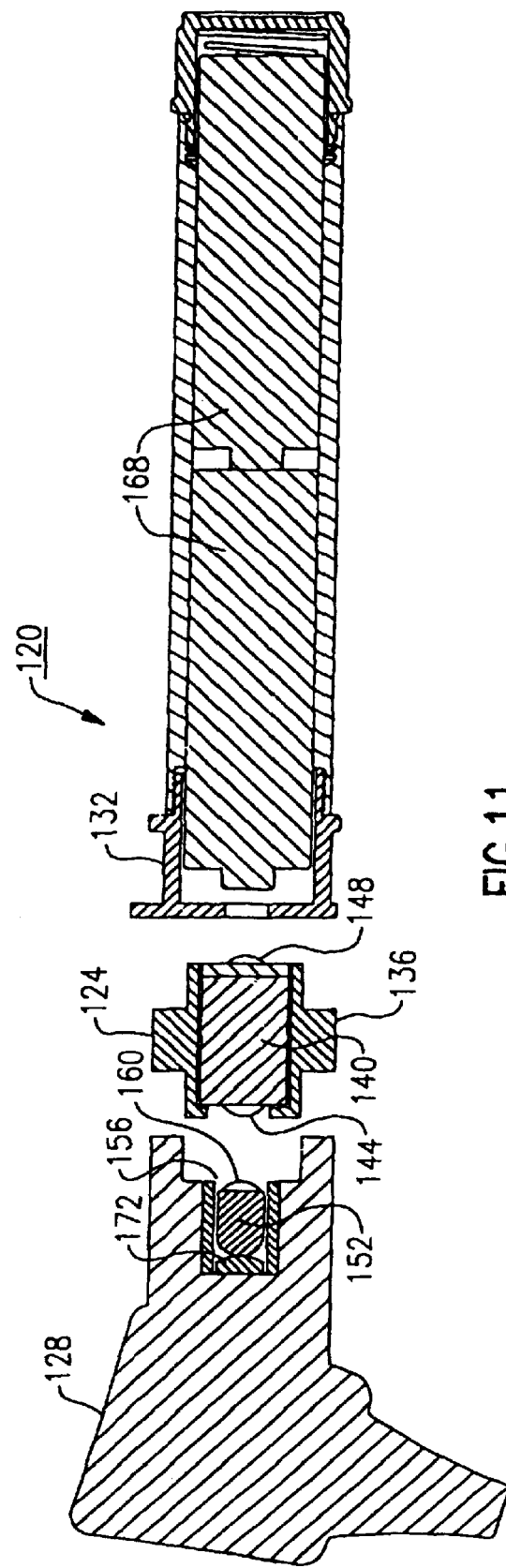
FIG. 11 is a side elevational view, partially in section, of a medical diagnostic instrument having an LED electrical adapter made in accordance with a preferred embodiment of the present invention.

While the above is a basis version, it should be noted that by including a resistor in series with the load, as shown in FIG. 10, rather than in parallel, this circuit represents a simplified current control, as represented in compensation block 100, FIG. 8. In addition, any other sensing means can be introduced such that the above circuit would respond to other changes such as light level, color, etc.

FIG. 9 includes a means for adequate energy storage in L1, FIG. 9, to bring the apparent source voltage to the LED above the forward voltage of the LED and then regulate the subsequent current which is drawn. Alternately, the regulator can be replaced by a low resistance MOSFET.

Including an oscillator to the design of the current compensation portion as in FIG. 9 would also permit dimming of the LED using either a duty cycle or a pulse width modulation technique. Since LEDs do not dim gradually and predictably with a decrease in voltage, use of the duty cycle would take advantage of the LEDs relatively fast "on/off" time to create "apparent" dimming for the user.

In addition, color will change as current is changed. Therefore, directly decreasing current to adjust light output, for example, will produce an undesirable variation in color. By utilizing either a duty cycle or pulse width modulation as a dimming "technique" for the LED, the LED is pulsed at virtually full power, but for shorter periods of time and therefore appears to dim. The current remains at the "normal" full on value during these pulses, therefore the color of the LED does not perceivably change as the LED is dimmed.

Depending on the degree of complexity and/or cost considerations, the oscillator can be replaced with a bimetallic element. This substitution also provides the opportunity to modify the light output by rapidly pulsing the LED at a duty cycle which represents the modified intensity desired.

Having described the basic circuitry and referring now to FIGS. 11–15, a number of potential locations for the herein described electrical LED adapter can be assumed, exemplary embodiments being herein described. For example and first referring to FIG. 11, there is illustrated a battery-powered diagnostic instrument 120, such as previously described in FIGS. 1 and 2, that further includes an adaptor module 124 carrying the electrical circuitry of FIGS. 9 and/or 10, the module being disposed between the instrument head 128 and the top of the handle 132. The adapter 124 includes a housing 136 including a resident printed circuit board 140 and respective electrical contacts 144, 148 provided at opposing ends of the housing. A white LED 152 such as described in U.S. Pat. No. 5,998,925, previously incorporated above, is disposed within a cavity 156 formed within the lower portion of the instrument head 128 wherein the LED includes at least one contact 160 that is placed in proximity with the upper facing contact 144 of the adapter 124. The lower facing contact 148 of the adapter 124 is arranged in relation to the retained batteries 168 disposed within the handle 132. A set of optics 172 are optionally disposed in relation to the LED die for coupling with the illumination output of the LED 152.

Figure 12:
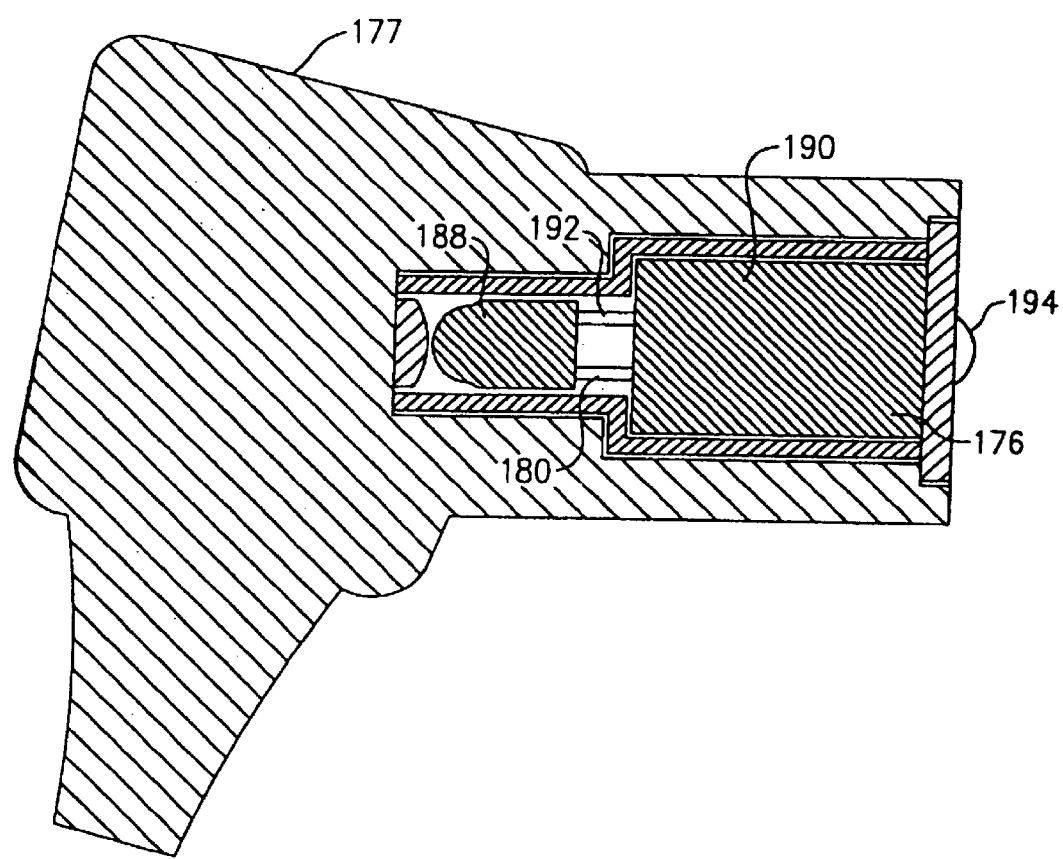
FIG. 12 is a side elevational view, partially in section, of a medical diagnostic instrument having an LED electrical adapter made in accordance with another preferred embodiment of the present invention.

Referring to FIG. 12, a similarly designed LED electrical adapter 176 can assume other locations relative to the medical diagnostic instrument. The adapter 176, according to this embodiment, is disposed within a cavity 180 formed within the interior of the instrument head 177 along with an LED 188 having contacts that engage a printed circuit board 190 having the circuitry previously described. The adapter 176 further includes a lower contact 194 that engages the batteries (not shown) provided in the handle (not shown).

Figure 15:
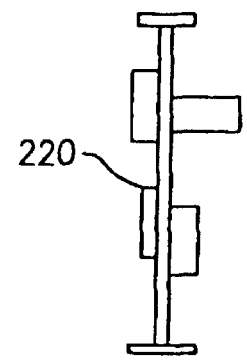
FIG. 15 is a side elevational view of a portion of the adapter of FIGS. 13 and 14.
Figure 14:
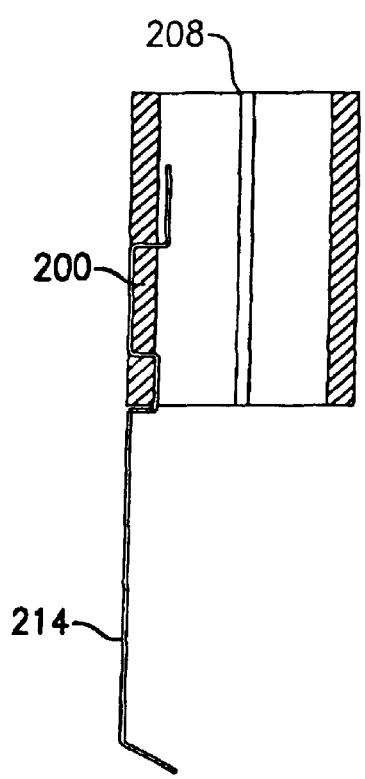
FIG. 14 is a side perspective view of the LED electrical adapter of FIG. 13.
Figure 13:
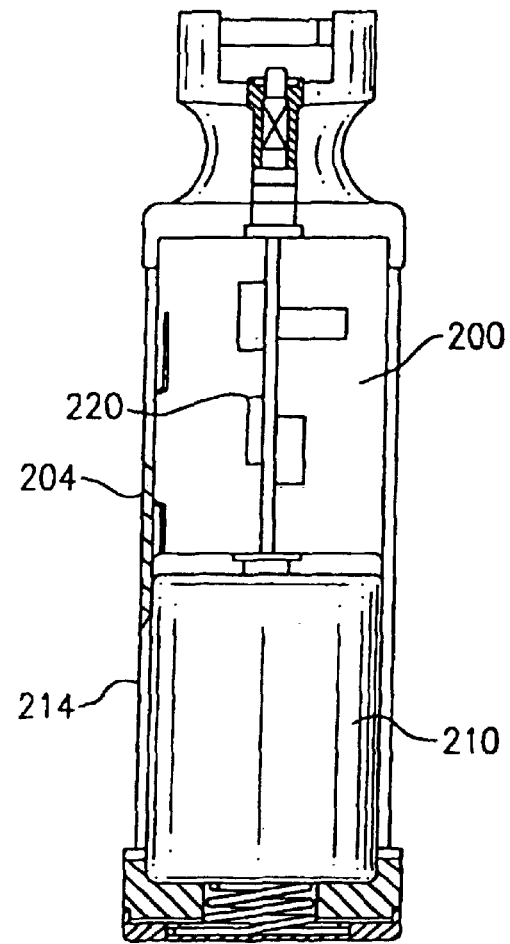
FIG. 13 is a side elevational partial perspective view of a LED electrical adapter for a medical diagnostic instrument made in accordance with yet another preferred embodiment of the present invention.

Referring to FIGS. 13–15, another embodiment of an LED electrical adapter is provided that includes a compact cartridge 200 that is sized so as to replace an existing battery typically retained within an instrument handle 204. The adapter cartridge 200 is preferably defined in a cylindrical shape and is sized similarly to that of a contained battery to permit fitting into the instrument handle 204 in lieu thereof. This electrical cartridge includes a slot 208 that retains specific voltage conversion means in the form of a voltage conversion means 220, having elements as defined above, the cartridge being disposed between one of the batteries 210 and the extending pin contact extending from the instrument head (not shown) as well as an extending negative contact strip 214 enabling a suitable electrical connection between the battery 210 and the LED (not shown). Each of the above assemblies can be retained in a housing (not shown for clarity) of convenient size.

In addition to and in complement of the herein described electrical adapter, an optical system can be added or modified to improve color. For example, a suitable filter and a collection lens can be placed at the light transmitting end of an LED having its top lens removed. The filter may also be part of this lens and the assembly may alternately be part of the LED or incorporated into part of the instrument head.

In addition to and in complement of the herein described electrical adapter, a means for detecting and switching the drive electronics from an LED version to an incandescent lamp version of a diagnostic instrument is beneficial, since this switching ability allows the same instrument to take advantage of each illumination system. There are several means for accomplishing this goal. The most basic technique is the incorporation of a mode switch which is manually actuated by the user of the instrument. This mode switch would connect the illumination to either the incandescent lamp drive circuitry or the LED drive circuitry based on the user's discretion.

Figure 12A:
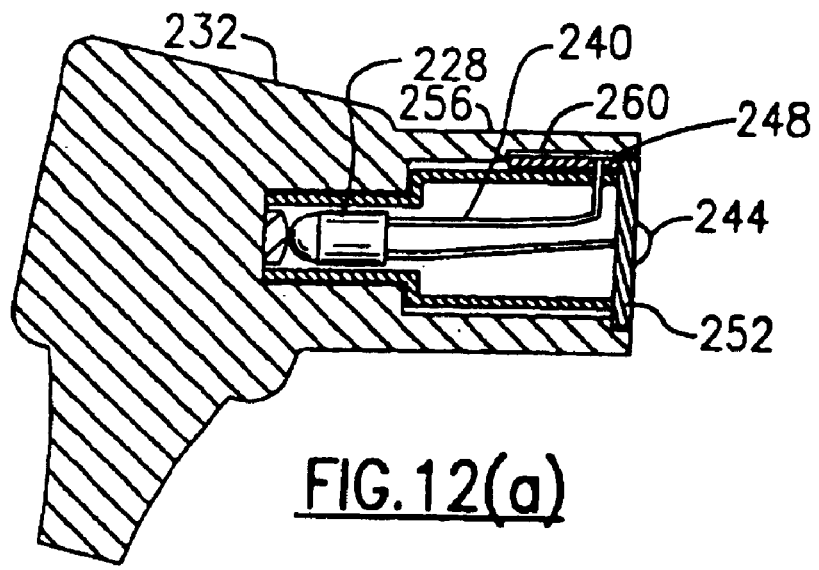
FIGS. 12(a) and 12(b) are side elevational views of a diagnostic instrument head, partially in section, including means for detecting the illumination mode of the head in accordance with a preferred embodiment of the present invention.
Figure 12B:
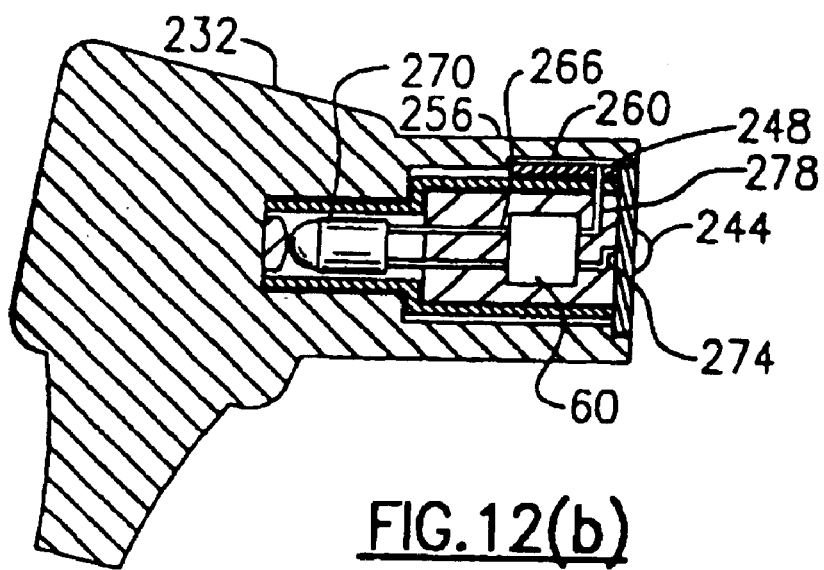

The operation of an exemplary switch configuration is depicted in FIGS. 12(a) and 12(b) showing alternative illumination sources as previously described. In FIG. 12(a), an incandescent lamp 228 is disposed in a diagnostic instrument head 232, such as an otoscope head, the incandescent lamp having leads 236, 240 extending to respective contact surfaces 244, 248. Contact surface 244 is located at the bottom of the lamp module 252 in a proximal end of the instrument head while contact surface 248 is located adjacent the lamp module 252. A third contact surface 256 is established along the exterior of the instrument head 232, this portion of the head being separated from contact surface 244 by an insulator 260.

The operation of the mode switch is based upon the combination of contact surfaces engaged. According to this embodiment, the incandescent lamp 228 is energized by supplying electrical energy from the handle or otherwise between contact surfaces 256 and 244, each of which are in direct contact with the lamp module 252.

In the embodiment of FIG. 12(b), on the other hand, an LED module 266 is situated in the instrument head 232 wherein the LED 270 is energized by supplying electrical energy between contact surfaces 244 and 248, each of which are in direct electrical contact with the LED module through respective electrical contacts 274 and 278 via electrical adapter 60.

As described, the adapter can provide a means for different contacts for the LED and the incandescent lamp, such that simply inserting the desired illumination device automatically selects the proper drive circuitry/configuration. In yet another alternative of the invention, the mechanical contact geometry can be the same for both illumination devices, and the adapter electronics can detect the presence or lack of polarity whether the illumination is an LED (polarized) or an incandescent bulb (not polarized). The above objective can be accomplished, in a preferred embodiment, using a microcontroller system such as illustrated in FIG. 16.

Figure 16:
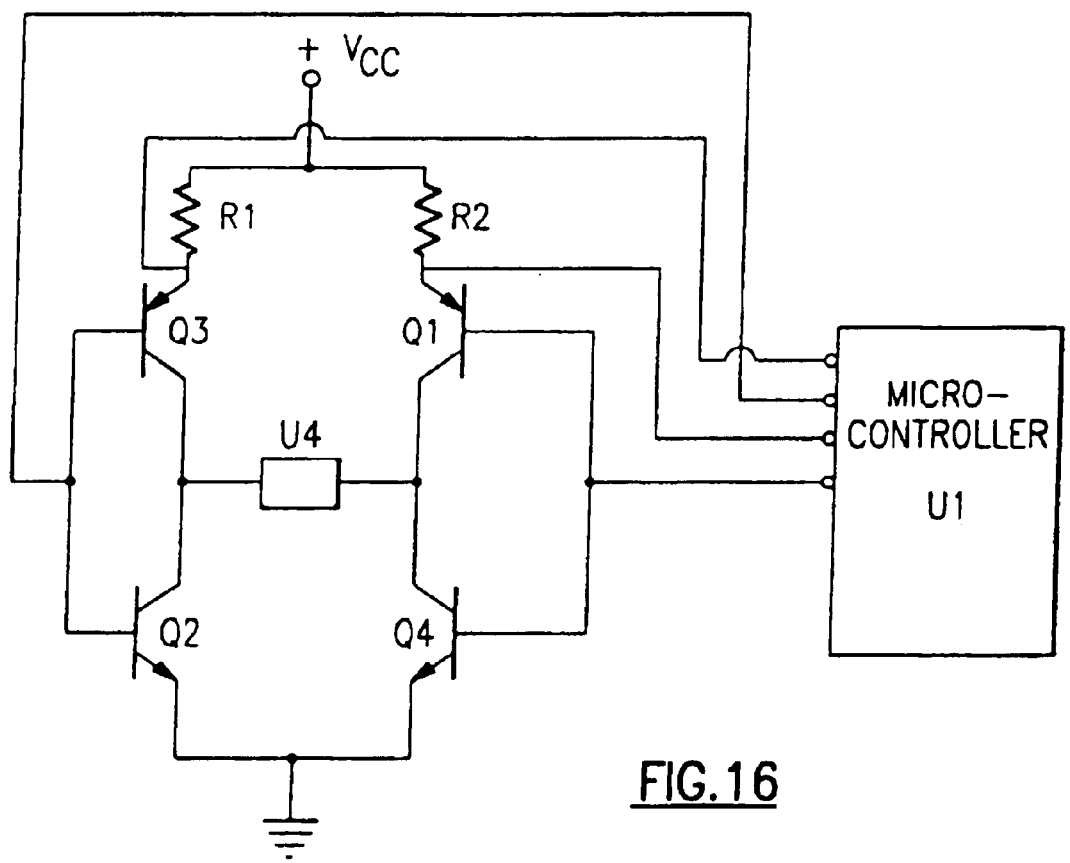
FIG. 16 is a circuit diagram of a microcontroller system for detecting the presence of an incandescent bulb or an LED.

Referring to FIG. 16, a microcontroller U1 turns on half H-bridges Q1/2 and Q3/4 sequentially and checks the resulting voltage at resistors R1 and R2. If the resulting voltage is the same, this provides an indicator that the current flow is symmetric in both directions, indicating a non-polarized illumination device and therefore the device located at U4 in this circuit would be determined to be an incandescent lamp. If the voltage is different between R1 and R2, the device would be determined to be polarized, indicating that the device located at U4 is an LED. In addition, the direction of polarity would also be known allowing the drive circuitry to be properly connected. One further benefit of the above detection scheme is that it would also allow detection of blown lamps or LED's if the current flow in each direction tested was found to be essentially zero. It is also noted that microcontroller U1 is presumed to include an analog to digital converter that is used to convert the analog voltage present at R1 and R2 to a digital reading. While there are several microcontrollers which have this feature, the analog to digital converter could be implemented separately if needed. Also, the drive circuitry and connection to U4 is intentionally left out of this diagram for the sake of simplicity and to convey the essential concepts of the invention. However it should be obvious to one of sufficient skill in the field that it can be accomplished even as simply as adding additional H-bridge sections (not shown) under microcontroller control.

Parts List for FIGS. 1–16
10 medical diagnostic instrument
10A, 10B diagnostic instrument
14 instrument handle
14A, 14B instrument handle
18 instrument head
18A, 18B instrument head
22 miniature halogen lamp
25 lamp housing
26 batteries
27 base
27A, 27B base
28A, 28B upper end
29 contact
30 adjustable voltage control
31 pin
32 ears
33 contact spring
36 light transmitting ends
37 ears
38 optical fibers
39 contact pin
40 tip portion
42 distal tip opening
44 bayonet
46 eyepiece
48 proximal end
50 instrument handle
52 cord
54 wall transformer
60 electrical LED adapter
64 LED package
84 AC or DC converter
100 current compensation portion
120 instrument
124 adaptor module
128 instrument head
132 handle
136 housing
140 printed circuit board
144 contact
148 contact
152 LED
156 cavity
160 contact
168 batteries
172 optics
176 adapter
177 instrument head
180 cavity
188 LED
190 printed circuit board
194 lower contact
200 cartridge 204 handle
208 slot
210 batteries
214 negative contact strip
220 voltage conversion means
228 incandescent lamp
232 instrument head
236 lead
240 lead
244 contact surface
248 contact surface
252 lamp module
256 contact surface
260 insulator
266 LED module
270 LED
274 electrical contact
278 electrical contact Though the following description has been made in terms of certain embodiments, it will be readily apparent that other modifications and variations are possible which encompass the spirit and scope of the herein claimed invention.

We claim:

1. An adapter for use with a medical diagnostic instrument originally configured with an incandescent lamp as an illumination source and a power supply specifically designed for powering said incandescent lamp, said adapter having means for permitting at least one LED to be used as the illumination source for said instrument and permitting said power supply to be used without alteration to enable energization of said at least one LED, and means for matching a polarity between said at least one LED and said power supply.

2. An adapter as recited in claim 1, wherein said at least one LED is a white LED.

3. An adapter as recited in claim 1, including means for limiting current supplied to said at least one LED by said power supply.

4. An adapter as recited in claim 3, including means for boosting the voltage supplied to said at least one LED by said power supply.

5. An adapter as recited in claim 1, including means for compensating current drawn by said at least one LED from said power supply.

6. An adapter as recited in claim 5, including means for boosting voltage supplied to said at least one LED by said power supply.

7. An adapter as recited in claim 1, wherein said adapter includes said at least one LED.

8. An adapter as recited in claim 1, including at least one optical element disposed in relation to said at least one LED used as the illumination source.

9. An adapter as recited in claim 8, including at least one optical filter disposed in relation to said at least one optical element.

10. An adapter as recited in claim 1, including means for compensating the color sense of said at least one LED.

11. An adapter as recited in claim 10, wherein said color sense compensating means includes means for boosting voltage supplied to at least one LED.

12. An adapter as recited in claim 1, including means for compensating voltage supplied to said at least one LED from said power supply.

13. An adapter as recited in claim 12, wherein said voltage compensating means includes means for boosting voltage supplied to said at least one LED.

14. An adapter as recited in claim 1, including means for compensating the light output of said at least one LED.

15. An adapter as recited in claim 14, wherein said light output compensating means includes means for boosting voltage supplied to said at least one LED.

16. An adapter as recited in claim 14, including means for dimming said at least one LED.

17. An adapter as recited in claim 10, including at least one optical filter.

18. A method for adapting a existing medical diagnostic instrument so as to incorporate at least one white LED as an illumination source, said existing instrument including a power supply for energizing a miniature incandescent bulb as an illumination source, said instrument including an existing instrument head and a existing instrument handle wherein said existing instrument head and said existing instrument handle include mating interconnecting ends which interlock said instrument head and said handle in a mechanical interconnection while simultaneously maintaining an electrical interface between said incandescent lamp and said power supply, said method including the steps of:

attaching an adapter between said instrument head and said instrument handle, said adapter including means for electrically interconnecting at least one LED and said power supply as well as means for mechanically interconnecting said instrument head and said instrument handle; and mounting said at least one LED in one of said adapter and said instrument head.

19. A method as recited in claim 18, including the step of attaching a new instrument head having said at least one LED to said adapter.

20. A method as recited in claim 18, including the steps of removing said incandescent bulb from said instrument head and mounting said existing instrument head onto said adapter, wherein said at least one LED is disposed in said adapter.

21. A diagnostic instrument comprising:

a power supply;

an incandescent light source disposed in said instrument that is powered by said power supply; and an adapter including at least one LED light source, said adapter having circuitry to permit said at least one LED light source to operate with said power supply when said adapter is attached to said instrument, said adapter being interchangeable with said incandescent light source to permit alternative operation of each said light source.

22. A method of using a diagnostic instrument, said method comprising the steps of:

providing an instrument with a releasably removable incandescent light source powered by a power supply;

removing the incandescent light source from the instrument; and attaching an interchangeable adapter having an LED light source and circuitry that operates with said power supply when said adapter is attached to said instrument to permit alternative operation of said instrument of each said light source.

23. In combination, an adapter for use with a medical diagnostic instrument, said instrument including a power supply that is electrically configured for solely powering an instrument having an incandescent lamp as an illumination source, said medical diagnostic instrument including an instrument head, a hand-grippable handle and at least one LED disposed in said instrument as the illumination source thereof, said adapter including means for electrically and mechanically interconnecting said power supply, and said at least one LED to enable said at least one LED to be used as said illumination source of said instrument and for effectively energizing said at least one LED, said adapter being independently attached between said instrument head and said hand-grippable handle and wherein said instrument head and said hand-grippable handle further include interconnect means for interconnecting said instrument head to said handle for providing a mechanical interface and maintaining an electrical interface between said power supply and an incandescent lamp when an incandescent lamp is typically used in the instrument, and in which said adapter includes respective ends adapted to connect to said interconnect means to provide said mechanical interface while creating an electrical interface between said power supply and said at least one LED.

24. A combination as recited in claim 23, wherein said adapter is independently attached between said instrument head and said band-grippable handle.

25. A combination as recited in claim 23, wherein said at least one LED is part of an LED module.

26. A combination as recited in claim 25, wherein said adapter is disposed in said LED module.

27. A combination as recited in claim 25, wherein said module includes at least one optical element disposed in relation to the output of said LED.

28. A combination as recited in claim 23, wherein said at least one LED is disposed in at least a portion of the instrument head.

29. A combination as recited in claim 23, wherein said least one LED is disposed in at least a portion of the adapter.

30. In combination, an adapter for use with a medical diagnostic instrument, including a power supply that is electrically configured for solely powering an instrument having an incandescent lamp as an illumination source, said medical diagnostic instrument including an instrument as the illumination source thereof, said adapter including means for electrically and mechanically interconnecting said power supply and said at least one LED to enable said at least one LED to be used as said illumination source of said instrument and for effectively energizing said at least one LED, wherein said adapter permits said at least one LED to be energized by said power supply without modification thereof wherein said instrument includes at least one of at least one LED and an incandescent lamp as the illumination source, said combination further including means for selectively activating said adapter depending on the illumination source provided in said instrument, including means for sensing the type of illumination source in said instrument.

31. A combination as recited in claim 23, wherein said adapter permits said at least one LED to be energized by said power supply without modification thereof.

32. A combination as recited in claim 30, wherein said adapter is disposed in at least a portion of said instrument head.

33. A combination as recited in claim 30, wherein said adapter is disposed in at least a portion of the hand-grippable handle.

34. A combination as recited in claim 30, including mode switching means connected to said adapter for enabling said adapter if at least one LED is used as the instrument illumination source.

35. A combination as recited in claim 30, wherein said illumination source sensing means includes means for sensing whether there is a polarity difference between said power supply and the illumination source and means for automatically enabling said adapter if there is a sensed polarity difference.

36. A combination as recited in claim 33, wherein said handle is modified to permit use of said at least one LED.

37. A combination as recited in claim 30, wherein said adapter is disposed in at least a portion of the power supply of said instrument.

38. A combination as recited in claim 30, wherein said at least one LED is a white LED.

39. A combination as recited in claim 30, wherein said at least one LED is disposed in at least a portion of an LED module.

40. A combination as recited in claim 39, wherein said LED module is disposed in at least a portion of said instrument head.

41. A combination as recited in claim 39, wherein said LED module is disposed in at least a portion of said adapter.

42. A combination as recited in claim 30, wherein said at least one LED is disposed in at least a portion of the instrument head.

43. A method for adapting a medical diagnostic instrument for use with at least one LED as an illumination source, said instrument including a power supply typically only electrically configured for energizing an incandescent lamp as an illumination source, said method comprising the steps of:
adding an adapter to at least one of an instrument head, an instrument handle and said instrument power supply and electrically connecting said adapter to said power supply and said at least one LED to energize same without modification to said power supply; and
matching the polarity between said at least one LED and said power supply.

44. A method as recited in claim 43, including the step of independently attaching an adapter between said instrument head and said handle.

45. A method as recited in claim 43, including the step of disposing said at least one LED into at least a portion of said adapter.

46. A method as recited in claim 43, including the step of limiting current supplied to said at least one LED by said power supply.

47. A method as recited in claim 43, including the step of adjusting voltage supplied to said at least one LED by said power supply.

48. A method as recited in claim 43, including the step of compensating current drawn by said at least one LED from said power supply.

49. A method as recited in claim 47, including the step of boosting voltage supplied to said at least one LED by said power supply.

50. A method as recited in claim 44, wherein said at least one LED is part of an LED module and in which said method includes the step of disposing said adapter in at least a portion of said LED module.

51. A method as recited in claim 44, including the step of providing a mechanical interface between said instrument head and said instrument handle that maintains an electrical interface between said power supply and said at least one LED, said at least one LED being located in one of the instrument head and the adapter.

52. A method as recited in claim 43, including the step of compensating the color sense of said at least one LED.

53. A method as recited in claim 52, wherein said color sense compensating step includes the step of boosting voltage of said at least one LED.

54. A method as recited in claim 52, including the step of optically filtering said at least one LED.

55. A method as recited in claim 43, including the step of compensating voltage supplied to said at least one LED from said power supply.

56. A method as recited in claim 55, wherein said voltage compensating step includes the step of boosting voltage supplied to said at least one LED.

57. A method as recited in claim 43, including the step of compensating the light output of said at least one LED.

58. A method as recited in claim 57, wherein said light output compensating step includes the step of boosting voltage supplied to said at least one LED.

59. A method as recited in claim 57, including the step of dimming said at least one LED.

60. A method as recited in claim 43, including the step of coupling at least one optical element in relation to the output of said at least one LED.

61. A method as recited in claim 60, including the step of placing at least one optical filter in relation to said at least one optical element.

62. A method for adapting a medical diagnostic instrument for use with at least one LED as an illumination source, said instrument including a power supply typically only electrically configured for energizing an incandescent lamp as an illumination source, said method comprising the steps of:

adding an adapter to at least one of an instrument head, and instrument handle and said instrument power supply and electrically connecting said adapter to said power supply and said at least one LED to energize same without modification to said power supply, wherein said instrument includes at least one of at least one LED and an incandescent lamp as the illumination source for said instrument, said method further including the additional steps of selectively activating said adapter depending on the illumination source provided in said instrument and of sensing the illumination source in said instrument.

63. A method as recited in claim 62, including the step of limiting current to said at least one LED from said power supply.

64. A method as recited in claim 62, including the step of compensating current drawn by said at least one LED from said power supply.

65. A method as recited in claim 63, including the step of boosting voltage supplied to said at least one LED from the power supply.

66. A method as recited in claim 64, including the step of boosting voltage supplied to said at least one LED from the power supply.

67. A method as recited in claim 62, including the step of independently attaching an adapter between said instrument head and said handle.

68. A method as recited in claim 67, wherein said at least one LED is part of an LED module and in which said method includes the step of disposing said adapter in at least a portion of said LED module.

69. A method as recited in claim 62, including the step of disposing said at least one LED into at least a portion of said adapter.

70. A method as recited in claim 69, wherein said illumination sensing step includes the additional steps of determining if there is a polarity difference between said power supply and the illumination source and automatically enabling raid adapter if there is a sensed polarity difference.

71. A method as recited in claim 62, including the step of compensating the light output of said at least one LED.

72. A method as recited in claim 71, wherein said light output compensating step includes the step of boosting voltage supplied to said at least one LED.

73. A method as recited in claim 71, including the step of dimming said at least one LED.

74. A method as recited in claim 62, including the step of compensating the color sense of said at least one LED.

75. A method as recited in claim 74, wherein said color compensating step includes the step of boosting voltage of said at least one LED.

76. A method as recited in cliam 75, including the step of optically filtering said at least one LED.

77. A method as recited in claim 62, including the step of compensating voltage supplied to said at least one LED from said power supply.

78. A method as recited in claim 77, wherein said voltage compensating step includes the step of boosting voltage supplied to said at least one LED.

79. A method as recited in claim 62, including the step of coupling at least one optical element in relation to the output of said at least one LED.

80. A method as recited in claim 79, including the step of placing at least one optical filter in relation to said at least one optical element.

* * * * *